(12) United States Patent
Koketsu et al.

(10) Patent No.: US 10,488,187 B2
(45) Date of Patent: Nov. 26, 2019

(54) MEMBER INSPECTION DEVICE AND MEMBER REPAIRING METHOD

(71) Applicant: MITSUBISHI HEAVY INDUSTRIES, LTD., Tokyo (JP)

(72) Inventors: Yoshihiro Koketsu, Tokyo (JP); Yoichiro Ara, Tokyo (JP); Yuuko Ujihara, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 16/070,935

(22) PCT Filed: Jan. 23, 2017

(86) PCT No.: PCT/JP2017/002153
§ 371 (c)(1),
(2) Date: Jul. 18, 2018

(87) PCT Pub. No.: WO2017/154383
PCT Pub. Date: Sep. 14, 2017

(65) Prior Publication Data
US 2019/0041199 A1  Feb. 7, 2019

(30) Foreign Application Priority Data

Mar. 9, 2016 (JP) ................. 2016-045984

(51) Int. Cl.
*G01B 11/30* (2006.01)
*G01N 21/84* (2006.01)
(Continued)

(52) U.S. Cl.
CPC ......... *G01B 11/30* (2013.01); *G01N 21/8422* (2013.01); *G01N 21/8851* (2013.01);
(Continued)

(58) Field of Classification Search
CPC ......... G01B 11/02; G01B 11/24; G01B 11/28; G01B 11/30; B05D 5/005; G01N 21/84;
(Continued)

(56) References Cited

U.S. PATENT DOCUMENTS 4,737,846 A     4/1988 Tokuno et al.
4,804,562 A *   2/1989 Ferguson ............... B22C 9/10
                                                427/140

(Continued)

FOREIGN PATENT DOCUMENTS

DE     10248943 A1    4/2004
EP      0668331 A1    8/1995
(Continued)

OTHER PUBLICATIONS

International Search Report and Written Opinion of International Application No. PCT/JP2017/002153 dated Apr. 11, 2017; 18 pp.
(Continued)

*Primary Examiner* — Gordon J Stock, Jr.
(74) *Attorney, Agent, or Firm* — Hauptman Ham, LLP (57) ABSTRACT

In a member inspection device and a member repairing method, an irradiation device irradiates a surface of a member to be inspected with light, an image pickup device picks up an image of a surface portion irradiated with the light, a failure detection device detects a failure area on the basis of a photographed image picked up by the image pickup device, and a determining device classifies the shape of the failure area detected by the failure detection device.

3 Claims, 5 Drawing Sheets

(51) Int. Cl.
*G01N 21/88* (2006.01)
*G01N 21/892* (2006.01)
*B05D 5/00* (2006.01)

(52) U.S. Cl.
CPC ........... *G01N 21/892* (2013.01); *B05D 5/005* (2013.01); *G01N 21/8803* (2013.01); *G01N 2021/888* (2013.01); *G01N 2021/8854* (2013.01)

(58) Field of Classification Search
CPC ............... G01N 21/8422; G01N 21/88; G01N 21/8803; G01N 21/8851; G01N 21/892; G01N 21/898; G01N 21/95; G01N 21/9515; G01N 2021/8411; G01N 2021/8416; G01N 2021/8427; G01N 2021/8472; G01N 2021/8854; G01N 2021/8864; G01N 2021/887; G01N 2021/8874; G01N 2021/888; G01N 2021/8887; G01N 2021/8918; G01N 2021/8924; G01N 2021/8925; G01N 2021/9518
USPC ............................ 356/600–613, 237.1–237.5
See application file for complete search history.

(56) References Cited

U.S. PATENT DOCUMENTS

| | | | |
|---|---|---|---|
| 5,237,404 A | 8/1993 | Tanaka et al. | |
| 5,239,487 A * | 8/1993 | Horejsi | G06Q 10/06 702/184 |
| 5,438,525 A * | 8/1995 | Shimbara | B62D 65/005 118/671 |
| 5,632,307 A * | 5/1997 | Fawley | F16L 55/1686 138/97 |
| 5,844,801 A * | 12/1998 | Kodama | B62D 65/005 700/110 |
| 5,922,399 A * | 7/1999 | Kobayashi | B05D 5/005 427/140 |
| 6,013,308 A * | 1/2000 | Saito | B05D 5/00 118/670 |
| 6,214,411 B1 | 4/2001 | Graefenhain-Thoma et al. | |
| 6,266,138 B1 * | 7/2001 | Keshavmurthy | G01B 11/303 356/237.2 |
| 6,320,654 B1 * | 11/2001 | Alders | G01N 21/8806 356/237.2 |
| 6,398,870 B1 | 6/2002 | Kaya et al. | |
| 6,714,831 B2 * | 3/2004 | Matthews | B05D 5/005 356/237.2 |
| 7,039,485 B2 * | 5/2006 | Engelbart | B29C 70/386 156/379 |
| 7,230,695 B2 * | 6/2007 | Ikuta | B82Y 10/00 356/237.2 |
| 7,499,812 B2 * | 3/2009 | Ersue | G01B 11/30 250/559.25 |
| 7,639,349 B2 * | 12/2009 | Ersue | G01N 21/9515 356/237.1 |
| 7,790,288 B2 * | 9/2010 | Perez | B05D 7/222 428/35.7 |
| 9,031,734 B2 * | 5/2015 | Froom | G01M 5/0016 701/29.3 |
| 9,149,835 B2 * | 10/2015 | Swarup | B05D 7/14 |
| 9,409,206 B2 * | 8/2016 | Berry | B05D 1/32 |
| 10,144,126 B2 * | 12/2018 | Krohne | B25J 11/005 |
| 10,192,367 B2 * | 1/2019 | Ko | G06F 1/163 |
| 2002/0132044 A1 * | 9/2002 | Quarles | B05D 5/005 427/140 |
| 2003/0139836 A1 | 7/2003 | Matthews et al. | |
| 2006/0164647 A1 * | 7/2006 | Shibata | G01N 21/89 356/430 |
| 2012/0109660 A1 * | 5/2012 | Xu | G06Q 21/89 356/430 |
| 2013/0129913 A1 * | 5/2013 | Yan | B05D 5/005 427/8 |
| 2017/0148102 A1 * | 5/2017 | Franke | G06Q 10/20 |

FOREIGN PATENT DOCUMENTS

| | | |
|---|---|---|
| EP | 0997201 A2 | 5/2000 |
| JP | S62279931 A | 12/1987 |
| JP | 4171077 A | 6/1992 |
| JP | 4301749 A | 10/1992 |
| JP | 2000337840 A | 12/2000 |
| JP | 2007275699 A | 10/2007 |
| JP | 2015160184 A | 9/2015 |
| WO | 2008092800 A1 | 8/2008 |

OTHER PUBLICATIONS

Gareth Bradshaw, "Non-Contact Surface Geometry Measurement Techniques", Image Synthesis Group, Trinity College, Dublin, Ireland, Sep. 1, 1999; 25 pp.

Supplementary European Search Report for European Application No. 17762729.6 dated Dec. 17, 2018; 10pp.

\* cited by examiner

MEMBER INSPECTION DEVICE AND MEMBER REPAIRING METHOD

RELATED APPLICATIONS

The present application is a National Phase of International Application No. PCT/JP2017/002153 filed Jan. 23, 2017, and claims priority based on Japanese Patent Application No. 2016-045984 filed Mar. 9, 2016.

TECHNICAL FIELD

The present invention relates to a member inspection device for inspecting failures on surfaces of a variety of members constituting aircrafts, cars, or the like and a member repairing method that repairs detected failure portions.

BACKGROUND ART

Examples of the variety of members constituting aircrafts, cars, or the like include metal members, resin members, complex material members, and underlying coating and primary coating are carried out on the surfaces thereof after the members are processed to an intended shape. At this time, an inspection of whether or not there is a failure area on the surfaces of the members is carried out after the underlying coating or the primary coating. This inspection is carried out by a worker visually checking the coated surfaces of the members.

However, an inspection work visually carried out by a worker on a number of members individually is heavy labor, puts a heavy burden on the worker, and also extends work hours, which deteriorates the working efficiency. Therefore, automation of an inspection work of members is described in, for example, PTL 1. In a processing method of a work described in PTL 1, an inspection robot and a processing robot are respectively disposed in an inspection station in a conveyance line through which the work is conveyed and a processing station downstream of the inspection station, the inspection robot inspects the surface state of the work, and the inspection robot carries out marking on a processed portion in which a detected process is required.

CITATION LIST

Patent Literature

[PTL 1] Japanese Unexamined Patent Application Publication No. S62-279931

SUMMARY OF INVENTION

Technical Problem

In the above-described processing method of a work of PTL 1, the surface state of the work is inspected, and marking is carried out on a processed portion in which a detected process is required. However, for the processed portion in the work in which a process is required, a repairing method differs depending on the failure shape. For example, in a case in which the failure shape is a recessed portion shape, it is necessary to fill the recessed portion with a repairing material, and, in a case in which the failure shape is a protrusion shape, it is necessary to remove the protrusion by wearing. Therefore, in a case in which only marking is carried out on the processed portion in the work in which a process is required, afterwards, the worker needs to check the shape of the marked processed portion and select a repairing work, which creates a problem of a poor working efficiency.

The present invention has solved the above-described problem, and an object of the present invention is to provide a member inspection device and a member repairing method which improve the working efficiency in an inspection work or a repairing work.

Solution to Problem

A member inspection device of the present invention for achieving the above-described object includes an irradiation device that irradiates a surface to be inspected of a member with light, an image pickup device that picks up an image of an irradiated portion of the light on the surface to be inspected, a failure detection device that detects a failure area on the basis of a photographed image picked up by means of the image pickup device, and a determining device that classifies the shape of the failure area detected by means of the failure detection device.

Therefore, when the irradiation device irradiates the surface to be inspected of the member with light, the image pickup device picks up an image of the light-irradiated portion on the surface to be inspected, the failure detection device detects a failure area on the basis of the photographed image, and the determining device classifies the shape of the failure area. Therefore, it is possible to carry out marking or the like which differs depending on the shape of the failure area, and the worker can carry out the optimal repairing treatment suitable for the shape of the failure area by specifying the shape of the failure area, and consequently, it is possible to improve the working efficiency in an inspection work or a repairing work.

In the member inspection device of the present invention, a repairing material supply device that supplies a repairing material is provided, and, when the failure area is determined to be a recessed portion by the determining device, the repairing material supply device supplies a repairing material to the recessed portion.

Therefore, when the failure area is a recessed portion, the repairing material supply device supplies a repairing material to the recessed portion, and thus the worker can repair the failure area simply by arranging the shape of the repairing material supplied to the recessed portion, and it is possible to improve the working efficiency in a repairing work.

In the member inspection device of the present invention, when the failure area is determined to be a recessed portion by the determining device, the repairing material supply device supplies a repairing material to the recessed portion in an amount larger than a volume of the recessed portion.

Therefore, when the failure area is a recessed portion, the repairing material supply device supplies a repairing material to the recessed portion in an amount larger than the volume of the recessed portion, and thus the worker can repair the failure area simply by removing the repairing material raised from the recessed portion, and it is possible to improve the working efficiency in a repairing work.

In the member inspection device of the present invention, when the failure area is determined to be a recessed portion by the determining device, a volume of the recessed portion is measured, and the repairing material supply device supplies a repairing material to the recessed portion in an amount equal to or larger than the volume of the recessed portion.

Therefore, when the failure area is a recessed portion, the repairing material supply device supplies a repairing material to the recessed portion in an amount equal to or larger than the volume of the recessed portion, and thus there is no case in which the repairing material is insufficient or excessive compared to the recessed portion, and the worker can easily repair the failure area within a short period of time simply by arranging the shape of the recessed portion.

In the member inspection device of the present invention, a marking device that carries out marking on the failure area is provided, and, when the failure area is determined to be not a recessed portion by the determining device, the marking device carries out marking on the failure area.

Therefore, when the failure area is not a recessed portion, the worker can specify that the failure area has a failure shape other than a recessed portion by carrying out marking on the failure area and can rapidly carry out the optimal repairing treatment suitable for the shape of the failure area.

In addition, a member repairing method of the present invention has a step of irradiating a surface to be inspected of a member with light, a step of picking up an image of an irradiated portion with the light, a step of detecting a failure area on the basis of a photographed image, a step of determining whether or not the failure area is a recessed portion, and a step of supplying a repairing material to the recessed portion when the failure area is the recessed portion.

Therefore, the surface to be inspected of the member is irradiated with light, an image of the light-irradiated portion on the surface to be inspected is picked up, a failure area is detected on the basis of a photographed image, and, when the failure area is a recessed portion, a repairing material is supplied to this recessed portion. Therefore, the worker simply needs to arrange the shape of the repairing material supplied to the recessed portion which is the failure area, and consequently, it is possible to improve the working efficiency in an inspection work or a repairing work.

Advantageous Effects of Invention

According to the member inspection device and the member repairing method of the present invention, a failure area on a surface to be inspected of a member is detected, and a shape of the failure area is classified, and thus the worker can carry out the optimal repairing treatment suitable for the shape of the failure area by specifying the shape of the failure area, and consequently, it is possible to improve the working efficiency in an inspection work or a repairing work.

DESCRIPTION OF EMBODIMENTS

Hereinafter, a preferred embodiment of a member inspection device and a member repairing method of the present invention will be described in detail with reference to the accompanying drawings. Meanwhile, the present invention is not limited by this embodiment, and, in a case in which there is a plurality of embodiments, a combination of the respective embodiments is also considered to be in the scope of the present invention.

Figure 1:
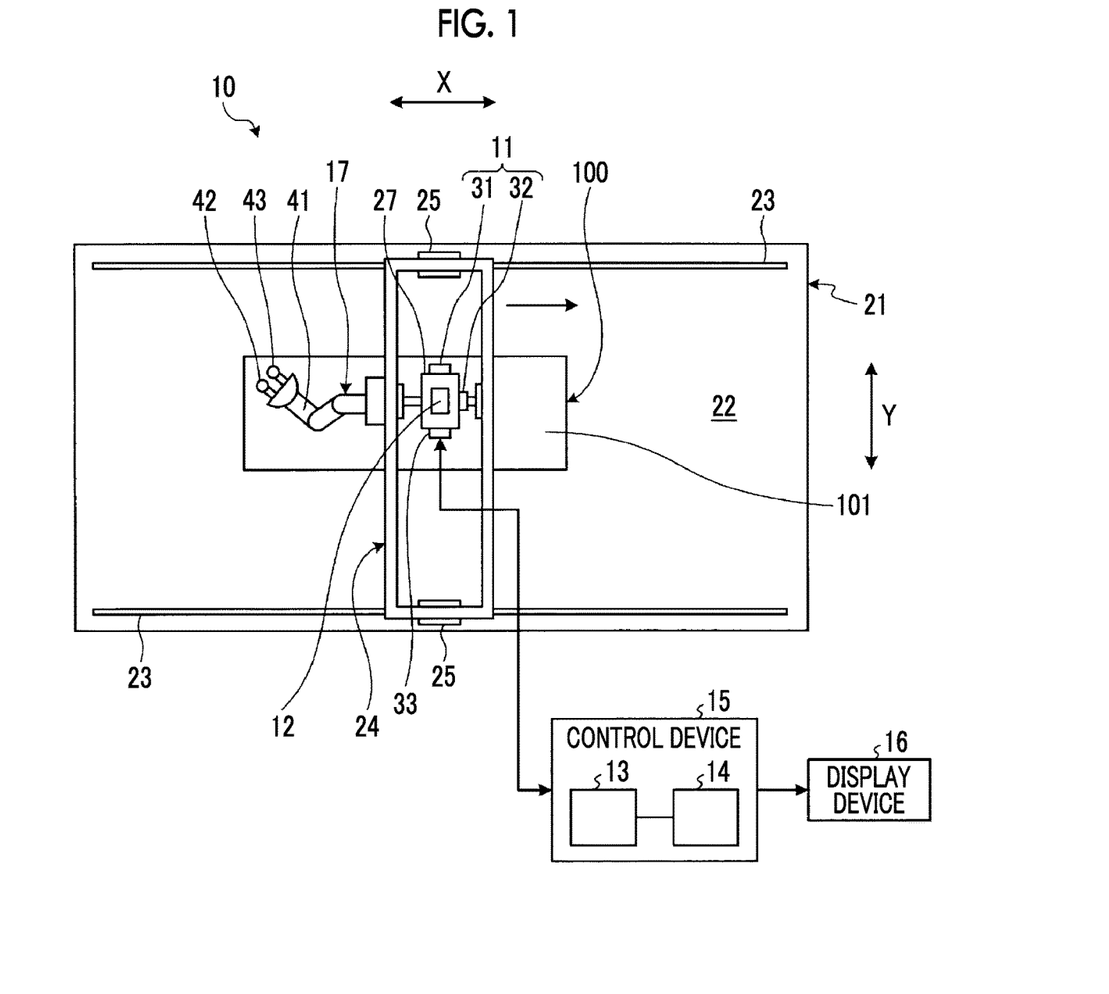
FIG. 1 is a plan view illustrating a member inspection device of the present embodiment.
Figure 2:
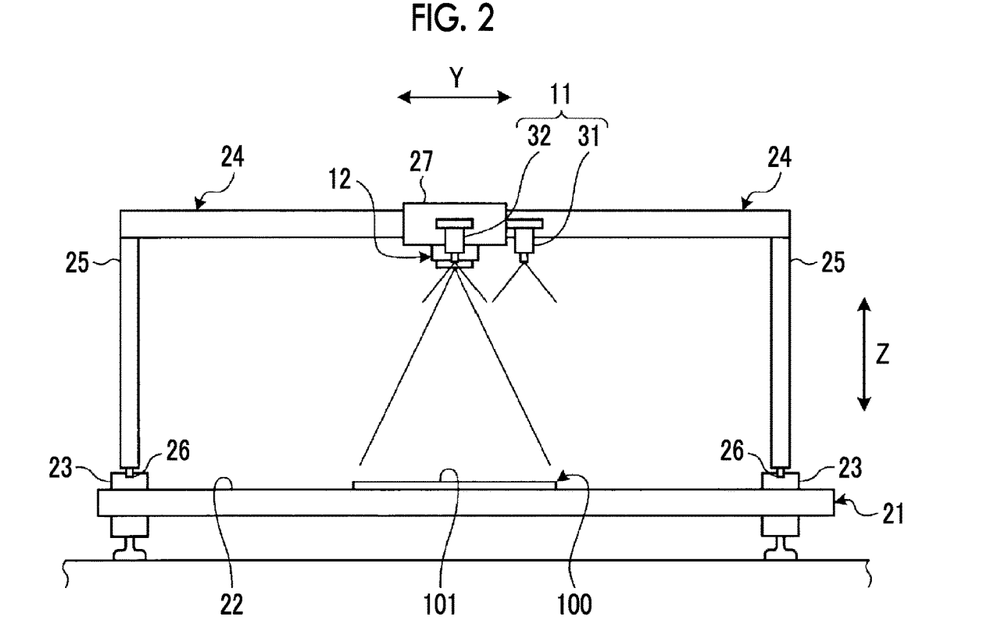
FIG. 2 is a front view illustrating the member inspection device.

FIG. 1 is a plan view illustrating a member inspection device of the present embodiment, and FIG. 2 is a front view illustrating the member inspection device.

In the present embodiment, a member inspection device 10 is a device that inspects a failure area on a surface to be inspected (surface) 101 of a member 100 as illustrated in FIG. 1 and FIG. 2. The member 100 is turned into a product by providing an underlying coating on the surface and then providing a primary coating thereon. The member inspection device 10 of the present embodiment detects a failure area on the surface of the member 100 on which underlying coating has been provided. The member inspection device 10 includes an irradiation device 11, an image pickup device 12, a control device 15 having a failure detection device 13 and a determining device 14, a display device 16, and a multi-jointed robot 17.

A support board 21 is installed parallel to a floor surface, a flat support surface 22 is formed on an upper surface portion, and the member 100 to be inspected can be mounted on the support surface 22. In addition, the support board 21 has guide rails 23 fixed along the longitudinal direction (X direction) on both sides in the width direction (Y direction). A moving body 24 forms a frame shape in a planar view and has leg portions 25 respectively provided on both sides in the width direction (Y direction), and guide members (for example, rollers) 26 respectively provided in the lower end portions of the respective leg portions 25 are movable along the guide rails 23. Therefore, the moving body 24 is movable along the support board 21 (in the X direction).

A supporting member 27 is fixed to the central portion of the moving body 24 and is movable integrally with the moving body 24. In the supporting member 27, the irradiation device 11 and the image pickup device 12 are mounted. The irradiation device 11 is a device that irradiates the surface to be inspected 101 of the member 100 with light. In this case, the irradiation device 11 is capable of irradiating the entire region of the surface to be inspected 101 of the member 100 with light.

The irradiation device 11 is constituted of a plurality (two in the present embodiment) of illuminators 31 and 32, and the illuminators 31 and 32 are provided in the outer circumferential portion of the supporting member 27. The illuminators 31 and 32 are capable of radiating light in two different directions. That is, the illuminator 31 is fixed to one side portion of the supporting member 27 in the Y direction and is capable of radiating light toward the support surface 22 at a predetermined irradiation angle toward the other side portion in the Y direction. The illuminator 32 is fixed to one side portion of the supporting member 27 in the X direction and is capable of radiating light toward the support surface 22 at a predetermined irradiation angle toward the other side portion in the X direction.

The image pickup device 12 is a device that picks up an image of a light-irradiated portion on the surface to be inspected 101. The image pickup device 12 is provided in the lower portion of the supporting member 27. In this case, the image pickup device 12 is capable of picking up an image across the entire region of the surface to be inspected 101 of the member 100. The image pickup device 12 is one (or the number thereof may be plural) line camera and picks up an image of the light-irradiated portion on the surface to be inspected 101.

Therefore, when the irradiation device 11 radiates light across the entire region of the surface to be inspected 101 of the member 100 at a predetermined irradiation angle, if there are recesses and protrusions on the surface to be inspected 101, the recesses and the protrusions are shown as shade and shadow. The image pickup device 12 picks up an image of the light-irradiated portion on the surface to be inspected 101 and thus picks up an image of shade and shadow generated by the protrusions and the recesses.

In the supporting member 27, an input and output portion 33 of the irradiation device 11 and the image pickup device 12 is provided. The input and output portion 33 is connected to the control device 15 through a cable or wirelessly and is capable of communicating a variety of data.

The control device 15 has the failure detection device 13 and the determining device 14. The failure detection device 13 is a device that detects a failure area on the basis of a photographed image picked up by means of the image pickup device 12, and the determining device 14 classifies the shape of the failure area detected by means of the failure detection device 13.

Figure 4A:
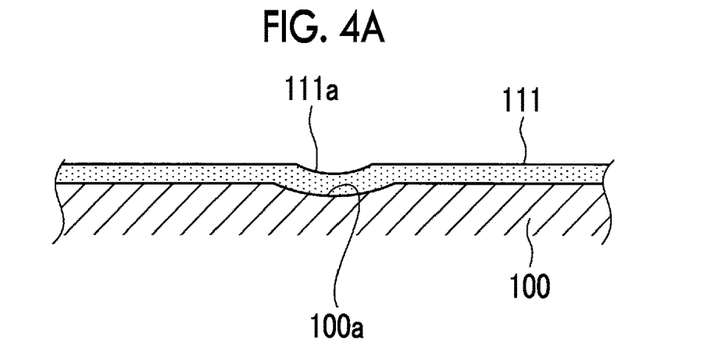
FIG. 4A is a schematic view illustrating a failure shape of a member.
Figure 4B:
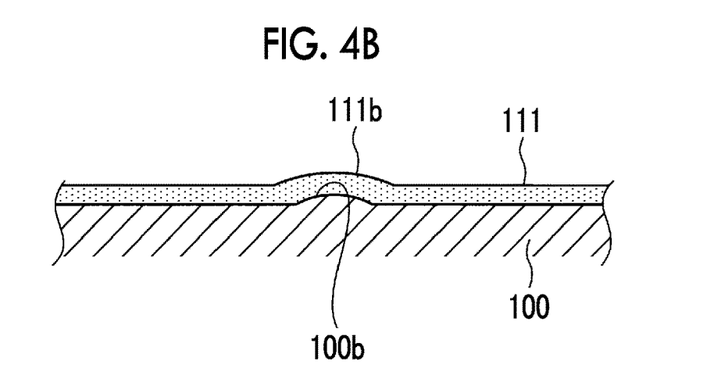
FIG. 4B is a schematic view illustrating a failure shape of the member.
Figure 4C:
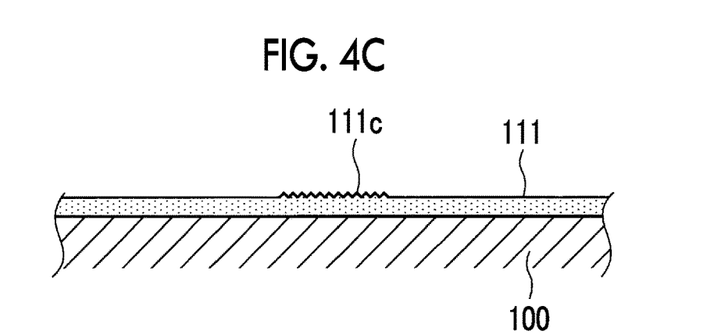
FIG. 4C is a schematic view illustrating a failure shape of the member.

FIG. 4A to FIG. 4C are schematic views illustrating failure shapes of the member. As failure areas that are formed on the surface to be inspected 101 of the member 100, a recessed portion, a protrusion, and a coating failure can be considered. When a recessed portion 100a is formed on the surface of the member 100 as illustrated in FIG. 4A, a recessed portion 111a is still shown on the surface even after an underlying coating 111 of a certain thickness is provided. In addition, when a protrusion 100b is formed on the surface of the member 100 as illustrated in FIG. 4B, a protrusion 111b is still shown on the surface even after the underlying coating 111 of a certain thickness is provided. Furthermore, when the surface of the member 100 is flat as illustrated in FIG. 4C, if the underlying coating 111 of a certain thickness is not provided, a fine protrusion and recessed portion 111c is shown on the surface.

The failure detection device 13 detects the recessed portion 111a, the protrusion 111b, and the protrusion and recessed portion 111c as failure areas on the basis of the photographed image picked up by means of the image pickup device 12. In addition, the determining device 14 determines whether the failure area detected by means of the failure detection device 13 is the recessed portion 111a or a different failure, that is, the protrusion 111b or the protrusion and recessed portion 111c.

Specifically, when the irradiation device 11 radiates light on the surface to be inspected 101 of the member 100 at a predetermined irradiation angle, protrusions and recesses on the surface to be inspected 101 are shown as shade and shadow. The image pickup device 12 picks up an image of the shade and shadow formed by the protrusions and the recesses and outputs the image to the control device 15. The failure detection device 13 detects the shade and shadow by means of, for example, a binarization treatment on the basis of the photographed image picked up by means of the image pickup device 12 and detects a failure area using the size of the shade and shadow. In this case, among the recessed portion 111a, the protrusion 111b, and the protrusion and recessed portion 111c, the size of the shade and shadow differs due to the length or depth thereof, and thus determining values of the size of shade and shadow that is determined as a failure area are set in advance by means of experiments. The failure detection device 13 detects a subject as a failure area when the size of the shade and shadow is larger than the determining value.

The determining device 14 carries out a determining treatment of the recessed portion 111a, the protrusion 111b, or the protrusion and recessed portion 111c depending on the shape or size of the shade and shadow detected as a failure area by means of the failure detection device 13. Specifically, between the recessed portion 111a and the protrusion 111b, the shape of shade and shadow differs. In addition, among the recessed portion 111a, the protrusion 111b, and the protrusion and recessed portion 111c, the size or number of shade and shadow differs. In this case as well, determining values of the sizes differentiating the recessed portion 111a, the protrusion 111b, and the protrusion and recessed portion 111c are set in advance by means of experiments. The determining device 14 determines a subject as the recessed portion 111a or the protrusion 111b when the size of shade and shadow is larger than the determining value or determines a subject as the protrusion and recessed portion 111c when the protrusion and recess shape continues in the shade and shadow.

The display device 16 is connected to the control device 15. The display device 16 displays the failure area detected by the failure detection device 13 and the recessed portion 111a, the protrusion 111b, or the protrusion and recessed portion 111c determined by the determining device 14. A worker checks whether or not the repairing of the member 100 is required from the displayed contents of the display device 16.

In addition, in the member inspection device 10, the multi-jointed robot 17 is mounted in the moving body 24. The multi-jointed robot 17 has a multi-jointed arm 41, and a repairing material supply gun (repairing material supply device) 42 and a marking gun (marking device) 43 are mounted in the tip portion of the multi-jointed arm 41. The repairing material supply gun 42 is capable of supplying an underlying coating material (repairing material) to the recessed portion 111a by means of spraying. The marking gun 43 is capable of spraying a marking material and carrying out marking the protrusion 111b or the protrusion and recessed portion 111c.

That is, the control device 15 is capable of controlling the multi-jointed robot 17 depending on the determination result of the determining device 14. When the failure area is the recessed portion 111a, the control device 15 supplies an underlying coating material to the recessed portion 111a using the repairing material supply gun 42. On the other hand, when the failure area is the protrusion 111b or the protrusion and recessed portion 111c, the control device 15 supplies a marking material to the protrusion 111b or the protrusion and recessed portion 111c using the marking gun 43.

In this case, when the failure area determined by means of the determining device 14 is the recessed portion 111a, the control device 15 supplies an underlying coating material to the recessed portion 111a using the repairing material supply gun 42 in an amount larger than the volume of the recessed portion 111a. In this case, the maximum volume of the recessed portion 111a that is formed as a failure area is found out by means of experiments or the like, the regulation amount to be supplied is set, and the repairing material supply gun 42 supplies the regulation amount of an underlying coating material to the recessed portion 111a. In addition, when the failure area determined by means of the determining device 14 is the recessed portion 111a, the control device 15 may estimate the volume of the recessed portion 111a from the size of the shade and shadow, set the regulation amount to be supplied from the estimated volume of the recessed portion 111a, and supply the regulation amount of an underlying coating material to the recessed portion 111a using the repairing material supply gun 42.

Figure 3:
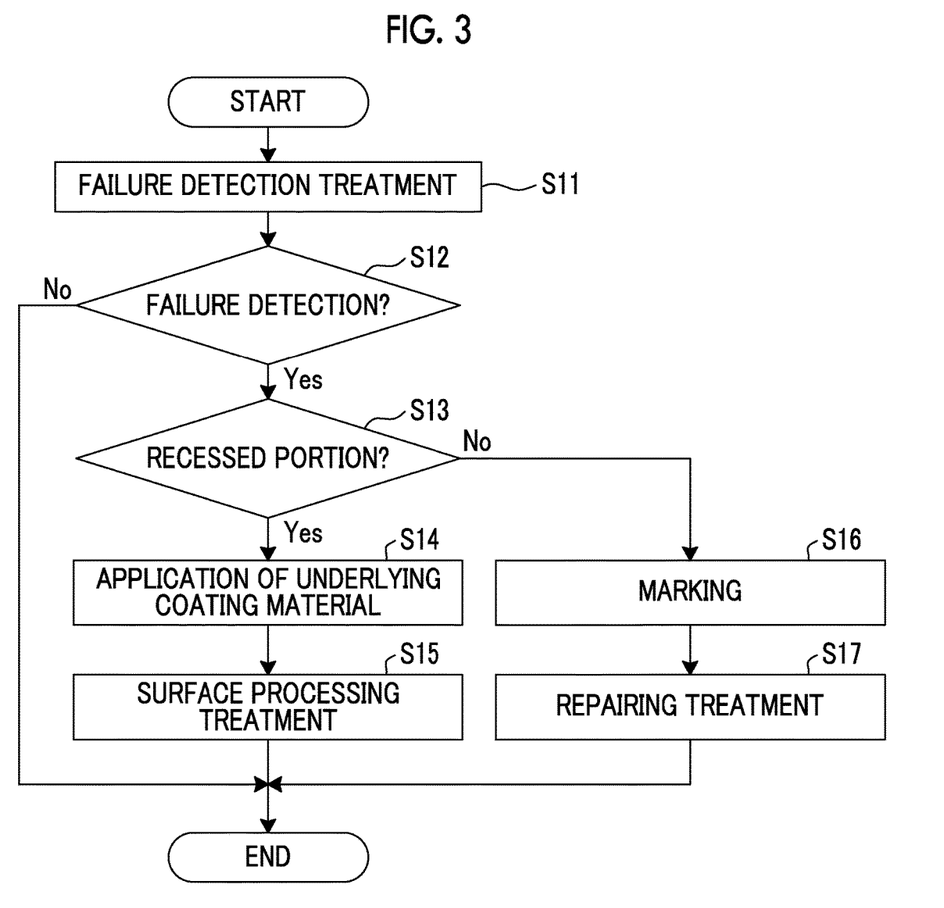
FIG. 3 is a flowchart illustrating a member inspection method.
Figure 5A:
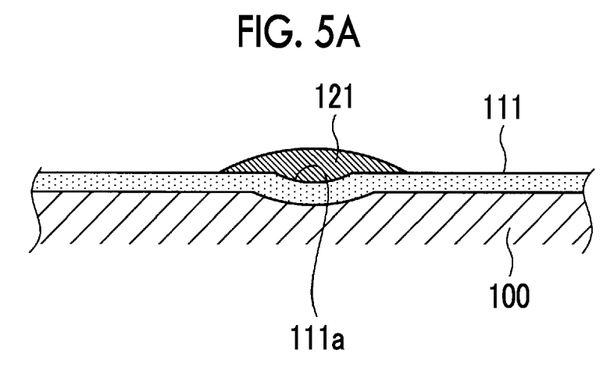
FIG. 5A is a schematic view illustrating a member repairing work.
Figure 5B:
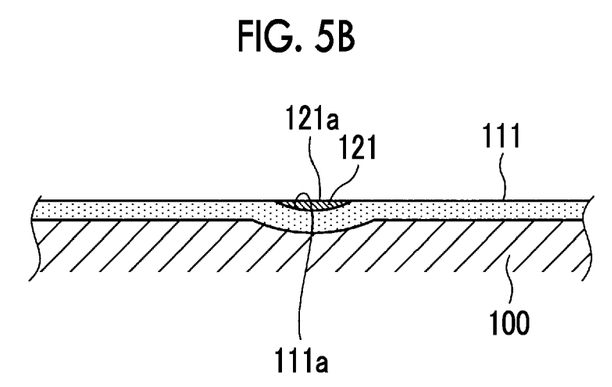
FIG. 5B is a schematic view illustrating a member repairing work.

Here, a member repairing method of the present embodiment will be described using a flowchart of FIG. 3. FIG. 3 is a flowchart illustrating the member inspection method, and FIG. 5A and FIG. 5B are schematic views illustrating a member repairing work.

The member repairing method of the present embodiment has a step of irradiating the surface to be inspected 101 of the member 100 with light, a step of picking up an image of a light-irradiated portion, a step of detecting a failure area on the basis of a photographed image, a step of determining whether or not the failure area is the recessed portion 111a, a step of supplying an underlying coating material to the recessed portion 111a when the failure area is the recessed portion 111a, and a step of supplying a marking material to the failure area when the failure area is not the recessed portion 111a.

As illustrated in FIG. 3, in Step S11, a failure detection treatment is carried out on the surface to be inspected 101 which is a surface of the member 100 provided with an underlying coating. That is, the moving body 24 is moved at a predetermined speed with respect to the support board 21, at this time, the irradiation device 11 irradiates the surface to be inspected 101 of the member 100 with light, and the image pickup device 12 picks up an image of this light-irradiated portion, and a photographed image is output to the control device 15 through the input and output portion 33.

In Step S12, the failure detection device 13 detects a failure area on the basis of the photographed image. Here, when the failure detection device 13 does not detect any failure area (No), the process does not follow the routine without doing anything. On the other hand, when the failure detection device 13 detects a failure area (Yes), in Step S13, the determining device 14 determines whether or not the detected failure area is the recessed portion 111a. Here, when the determining device 14 determines the failure area as the recessed portion 111a (Yes), in Step S14, the control device 15 supplies an underlying coating material to the recessed portion 111a using the repairing material supply gun 42.

That is, as illustrated in FIG. 5A, the repairing material supply gun 42 sprays an underlying coating material toward the recessed portion 111a, whereby an underlying coating material 121 fills the inside of the recessed portion 111a, and the recessed portion falls in a heaped state. In addition, in Step S15, a surface processing treatment of the surface to be inspected 101 of the member 100 is carried out, whereby the underlying coating material 121 protruding from the recessed portion 111a is removed, and a surface 121a of the underlying coating material 121 becomes equal to the surface of the member 100 as illustrated in FIG. 5B.

On the other hand, in Step S13, when the determining device 14 determines that the failure area is not the recessed portion 111a (No), in Step S16, the control device 15 supplies a marking material to the protrusion 111b or the protrusion and recessed portion 111c using the marking gun 43. In addition, in Step S17, a repairing treatment is carried out on the failure area. For example, the protruding underlying coating material is removed from the protrusion portion 111b, thereby making the protrusion portion even with the surface of the member 100. In addition, an underlying coating material is applied to the protrusion and recessed portion 111c as necessary, and the surface is polished, thereby making the protrusion and recessed portion even with the surface of the member 100.

As described above, in the member inspection device of the present embodiment, the irradiation device 11 that irradiates the surface to be inspected 101 of the member 100 with light, the image pickup device 12 that picks up an image of the light-irradiated portion on the surface to be inspected 101, the failure detection device 13 that detects a failure area on the basis of a photographed image picked up by means of the image pickup device 12, and the determining device 14 that classifies the shape of the failure area detected by means of the failure detection device 13 are provided.

Therefore, when the irradiation device 11 irradiates the surface to be inspected 101 of the member 100 with light, the image pickup device 12 picks up an image of the light-irradiated portion on the surface to be inspected 101, the failure detection device 13 detects a failure area on the basis of a photographed image, and the determining device 14 classifies the shape of the failure area. Therefore, it is possible to carry out different marking or the like depending on the shape of the failure area, the worker can carry out the optimal repairing treatment suitable for the shape of the failure area by specifying the shape of the failure area, and consequently, it is possible to improve the working efficiency in an inspection work or a repairing work.

In the member inspection device of the present embodiment, the repairing material supply gun 42 that supplies the underlying coating material 121 as a repairing material is provided, and, when the failure area is determined to be the recessed portion 111a, the control device 15 supplies the underlying coating material 121 to the recessed portion 111a using the repairing material supply gun 42. Therefore, the worker can repair the failure area simply by arranging the shape of the underlying coating material 121 supplied to the recessed portion 111a, and it is possible to improve the working efficiency in a repairing work.

In the member inspection device of the present embodiment, when the failure area is determined to be the recessed portion 111a, the control device 15 supplies the underlying coating material 121 to the recessed portion 111a using the repairing material supply gun 42 in an amount larger than the volume of the recessed portion 111a. Therefore, the worker can repair the failure area simply by removing the underlying coating material 121 raised from the recessed portion 111a, and it is possible to improve the working efficiency in a repairing work.

In the member inspection device of the present embodiment, when the failure area is determined to be the recessed portion 111a, the control device 15 measures the volume of the recessed portion 111a and supplies the underlying coating material 121 to the recessed portion 111a in an amount equal to or larger than the volume of the recessed portion 111a using the repairing material supply gun 42. Therefore, there is no case in which the underlying coating material 121 is insufficient or excessive compared to the recessed portion 111a, and the worker can easily repair the failure area within a short period of time simply by arranging the shape of the recessed portion 111a.

In the member inspection device of the present embodiment, the marking gun 43 that carries out marking on the failure area is provided, and, when the failure area is determined to be not the recessed portion 111a, the control device 15 carries out marking on the failure area using the marking gun 43. Therefore, the worker can specify that the failure area has a failure shape other than the recessed portion 111a and can rapidly carry out the optimal repairing treatment suitable for the shape of the failure area.

In addition, the member repairing method of the present embodiment has the step of irradiating the surface to be inspected 101 of the member 100 with light, the step of picking up an image of a light-irradiated portion, the step of detecting a failure area on the basis of a photographed image, the step of determining whether or not the failure area is the recessed portion 111a, and the step of supplying the underlying coating material 121 to the recessed portion 111a when the failure area is the recessed portion 111a.

Therefore, the worker simply needs to arrange the shape of the underlying coating material 121 supplied to the recessed portion 111a which is the failure area, and consequently, it is possible to improve the working efficiency in an inspection work or a repairing work.

Meanwhile, in the above-described embodiment, the underlying coating material 121 is used as the repairing material, but the present invention is not limited to this constitution, and a repairing material of a material that is different from the underlying coating material 121 may be used. In addition, in the present embodiment, the inspection is carried out on the surface to be inspected 101 of the member 100 which has been provided with the underlying coating, but the inspection may be carried out on the surface to be inspected 101 of the member 100 which has not yet been provided with the underlying coating, or the inspection is carried out on the surface to be inspected 101 of the member 100 which has been provided with the primary coating.

In addition, in the above-described embodiment, the member 100 is mounted on the support board 21, the moving body 24 in which the irradiation device 11 and the image pickup device 12 are mounted is moved with respect to the support board 21, and, at this time, the inspection is carried out on the surface to be inspected 101 of the member 100, but present invention is not limited to this constitution. For example, the inspection may be carried out on the surface to be inspected 101 by immovably fixing the supporting member 27 in which the irradiation device 11 and the image pickup device 12 are mounted, mounting the member 100 on the moving body 24 provided on the support board 21, and moving the member 100.

REFERENCE SIGNS LIST

10 MEMBER INSPECTION DEVICE
11 IRRADIATION DEVICE
12 IMAGE PICKUP DEVICE
13 FAILURE DETECTION DEVICE
14 DETERMINING DEVICE
15 CONTROL DEVICE
16 DISPLAY DEVICE
17 MULTI-JOINTED ROBOT
42 REPAIRING MATERIAL SUPPLY GUN (REPAIRING MATERIAL SUPPLY DEVICE)
43 MARKING GUN (MARKING DEVICE)
100 MEMBER
101 SURFACE TO BE INSPECTED
111 UNDERLYING COATING (REPAIRING MATERIAL)
111a RECESSED PORTION
111b PROTRUSION
111c PROTRUSION AND RECESSED PORTION
121 UNDERLYING COATING MATERIAL (REPAIRING MATERIAL)

The invention claimed is:

1. A member inspection device comprising:
an irradiator provided in an outer circumferential portion of a supporting member and configured to irradiate a surface to be inspected of a member with light;
an imager provided in a lower portion of the supporting member and configured to pick up an image of an irradiated portion of the light on the surface to be inspected;
a controller connected to an input and output portion of the irradiator and the imager provided in the supporting member and comprising:
  a failure detector configured to detect a failure area on the basis of a photographed image picked up by means of the imager;
  a determining circuit configured to classify a shape of the failure area detected by means of the failure detector;
a repairing material supplier configured to supply a repairing material; and
a marker configured to carry out marking on the failure area,
wherein, when the failure area is determined to be a recessed portion by the determining circuit, the repairing material supplier is further configured to supply the repairing material to the surface to be inspected of the recessed portion in an amount larger than a volume of the recessed portion so as to form a heaped state,
the irradiator is comprises a plurality of illuminators, and
the repairing material supplier and the marker are mounted in a tip portion of a multi-jointed arm of a multi-jointed robot.

2. The member inspection device according to claim 1, wherein when the failure area is determined to be not a recessed portion by the determining circuit, the marker is configured to carry out marking on the failure area.

3. A member repairing method comprising:
a step of irradiating a surface to be inspected of a member with light by a plurality of illuminators;
a step of picking up an image of an irradiated portion with the light;
a step of detecting a failure area on the basis of a photographed image;
a step of determining whether or not the failure area is a recessed portion;
a step of supplying a repairing material, by a repairing material supplier mounted in a tip portion of a multi-jointed arm of a multi-jointed robot, to the surface to be inspected of the recessed portion in an amount larger than a volume of the recessed portion so as to form a heaped state when the failure area is the recessed portion; and
a step of carrying out marking on the failure area by a marker mounted in the tip portion when the failure area is determined to be not the recessed portion.

* * * * *